US007507377B2

(12) United States Patent
Rousseau et al.

(10) Patent No.: US 7,507,377 B2
(45) Date of Patent: Mar. 24, 2009

(54) DEVICE FOR AUTOMATIC ANALYSIS OF A LIQUID SAMPLE

(75) Inventors: Alain Rousseau, Paris (FR); Khaled Abou-Saleh, Courbevoie (FR); Patrick Perin, Saint Cyr l'ecole (FR); Philippe Poutrel, Auvers sur Oise (FR)

(73) Assignee: Stago Instruments, Gennevilliers (FR)

( * ) Notice: Subject to any disclaimer, the term of this patent is extended or adjusted under 35 U.S.C. 154(b) by 277 days.

(21) Appl. No.: 10/503,239

(22) PCT Filed: Jan. 28, 2003

(86) PCT No.: PCT/FR03/00253

§ 371 (c)(1),
(2), (4) Date: Apr. 15, 2005

(87) PCT Pub. No.: WO03/065047

PCT Pub. Date: Aug. 7, 2003

(65) Prior Publication Data

US 2005/0175502 A1 Aug. 11, 2005

(30) Foreign Application Priority Data

Feb. 1, 2002 (FR) .................................. 02 01237

(51) Int. Cl.
*G01N 35/02* (2006.01)
*G01N 35/04* (2006.01)

(52) U.S. Cl. .......................... 422/102; 422/55; 422/58; 422/66; 422/82.05; 422/64; 436/43; 436/47; 436/49; 436/165

(58) Field of Classification Search .................. 422/55, 422/58, 65, 66, 82.05, 102; 436/43, 47, 49, 436/165
See application file for complete search history.

(56) References Cited

U.S. PATENT DOCUMENTS 3,999,949 A * 12/1976 Andersson et al. .......... 422/100
4,200,000 A * 4/1980 Fluehmann .................. 74/437
4,362,698 A * 12/1982 Boosalis et al. ............. 422/102

(Continued)

FOREIGN PATENT DOCUMENTS

EP 0 325 874 A 8/1989

(Continued)

OTHER PUBLICATIONS

Patent Abstracts of Japan vol. 007, No. 015 (P-169) (Jan. 21, 1983) & JP 57 171265 A (Raion KK) (Oct. 21, 1982).

(Continued)

*Primary Examiner*—Jill Warden
*Assistant Examiner*—P. Kathryn Wright
(74) *Attorney, Agent, or Firm*—Browdy and Neimark, P.L.L.C.

(57) ABSTRACT

This invention relates to a device usable in an automatical apparatus for the determination of the rate of change of the physical state of a medium. This device has a series of cuvettes having two opposites shoulders which extend in the plane of the opening of the cuvette and a flexible film which is fixed on the shoulders. This film is provided with a series of oblong opening respectively arranged above the cuvette openings. An optical detection station is provided which has a light source generating a light beam which illuminates the upper face of the cuvette bowls and an optoeleclectronic detector placed below the bottom of the bowls.

12 Claims, 2 Drawing Sheets

U.S. PATENT DOCUMENTS

| | | | | | |
|---|---|---|---|---|---|
| 4,731,225 | A | * | 3/1988 | Wakatake | 422/65 |
| 4,918,984 | A | * | 4/1990 | Martinoli et al. | 73/64.43 |
| 5,849,247 | A | * | 12/1998 | Uzan et al. | 422/65 |
| 5,942,441 | A | * | 8/1999 | Nylen | 436/179 |
| 6,328,164 | B1 | * | 12/2001 | Riekkinen et al. | 206/569 |
| 2001/0002986 | A1 | | 6/2001 | Fattinger et al. | |

FOREIGN PATENT DOCUMENTS

| | | | |
|---|---|---|---|
| EP | 0 642 830 | A | 3/1995 |
| EP | 0 837 331 | A | 4/1998 |
| EP | 0 904 841 | A | 3/1999 |
| WO | WO 99 64839 | A | 12/1999 |

OTHER PUBLICATIONS

Patent Abstracts of Japan vol. 008, No. 033 (P-254). (Feb. 14, 1984) & JP 58 189559 A (Tokyo Shibaura Denki KK) (Nov. 5, 1983).

Patent Abstracts of Japan vol. 008, No. 109 (P-275), (May 22, 1984) & JP 59 017160 A (Olympus Kogaku Kogyo KK) (Jan. 28, 1984).

Patent Abstracts of Japan vol. 016, No. 128 (C-0924) (Apr. 2, 1992) & JP 03 292880 A (Erumetsukusu:KK) (Dec. 24, 1991).

Patent Abstracts of Japan vol. 1999, No. 12 (Oct. 29, 1999) & JP 11 183484 A (Olympus Optical Co Ltd) (Jul. 9, 1999).

* cited by examiner

DEVICE FOR AUTOMATIC ANALYSIS OF A LIQUID SAMPLE

The present invention concerns a device for automatically analysing a liquid sample. It is more specifically but not exclusively aimed at improving an automatic device able to be used for determining the modification times of a medium in a physical state.

This device is particularly applicable to determining blood coagulation in accordance with a process according to which the blood sample is placed at the bottom of a bowl containing a ferromagnetic ball driven in a periodic movement under the effect of an external magnetic field. The modifications of the movements of the ferromagnetic ball (for example the amplitude and/or frequency variations), which are representative of changes of the physical state of the blood, are then detected with the aid of suitable means.

This type of device is described in the patent WO 99 64839 filed in the name of the Junior Instruments company.

It includes a bowl distributor for sole usage, each bowl comprising a bent inward bottom constituting the rolling path of the ball, and a face opposite the bottom having an opening. These bowls are placed side by side and fixed on a flexible film in such a way that they can be moved, said film sealing off their openings. The film equipped with bowls can be wound onto a coil able to be engaged on an element provided in a storage and distribution compartment of the device. The bowls run off one by one into a detection station.

As the support film seals off the openings of the bowl, a slit needs to be made by incision so as to allow the pipette to pass through. Once this is done, pressure is exerted on the film so as to disconnect the bowl.

Moreover, the presence of this slit renders the pipette operation more delicate with a risk of staining the film.

In addition, the presence of the film implies the use of a powerful light source and the homogeneity of the beam generated by this source through the bowl shall be disturbed by both the presence of the slit and any possible stains present on the film. Moreover, the heterogeneous medium traversed by the beam generated by the source generates multiple reflections, especially against the walls and edges of the bowls, which risks falsifying the analysis of the movement of the ferromagnetic ball.

Therefore, the object of the invention is to resolve these drawbacks.

To this effect, it concerns a device for the automated analysis of a liquid sample, said device comprising a series of bowls for sole usage, each comprising a bottom, one upper face opposite the bottom having one opening and two opposing shoulders extending on both sides of the bowl approximately inside the plane of the opening, the bowls being placed side by side and joined to each other by a flexible film secured to said shoulders and covering, at least partially, the openings of said bowls. According to the invention, this device is characterised in that the film has a series of orifices situated respectively at the right of the openings of the bowls.

The device may comprise an optical detection station introducing a light source, for example infrared, illuminating the upper face of the bowl and an opto-electronic detector placed below the bottom, the aim of the light being intended to allow reading of the movement of the ball via opto-electronic detection.

In this case, the film can be made from a diffusing material for the infrared light rendering the lighting luminous beam more homogeneous. The dimensions of the orifice shall then be determined in particular according to the dimensions of the pipette, its position and the sought-after homogeneity of the intensity of the luminous beams traversing a predetermined effective volume of the bowl.

In a case where the device determines the modification times of the physical state of a sample contained in the bowl by detecting the movements of a ball moving on the bottom of the bowl, said orifice could have the shape of an oblong opening centered partially on the rolling path of the ball and whose width is slightly smaller than the diameter of the ball.

Advantageously, the material constituting the film could have liquid absorption properties, such as pores, so as to fix any possible projections of liquid and of therefore reducing the risks of contamination of the samples contained in the bowls adjacent to the bowl currently being analysed.

This device could also comprise a pipette station introducing a pipette moving transversally with respect to the reeling off axis of the bowls. So as to mitigate an inaccuracy of the movement of the pipette, applying said pipette to the film or its edges possibly resulting in the falling out of step unhooking of the bowls and/or the projections, the orifices of the film extending along an axis transversal to said reeling off axis of the bowls.

Moreover, this device could comprise a station for cutting the analysed bowls so as to receive them in a single container.

It is to be noted that this bowls/film unit remains adaptable to already existing models.

One embodiment of the invention is described hereafter and is given by way of non-restrictive example with reference to the accompanying drawings on which:

In this example, the automatic analysis device 1 introduces a bowl feed comprising a series of about one hundred bowls forming a strip 2.

Figure 2:
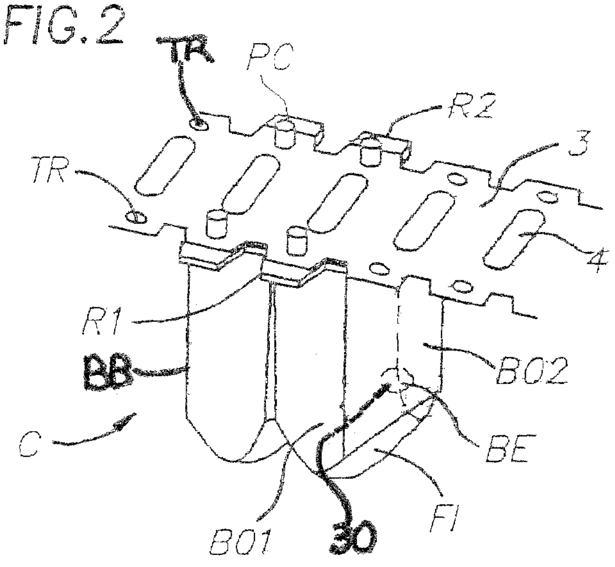
FIG. 2 is a diagrammatic perspective view of a bowl mounted on the film.
Figure 3:
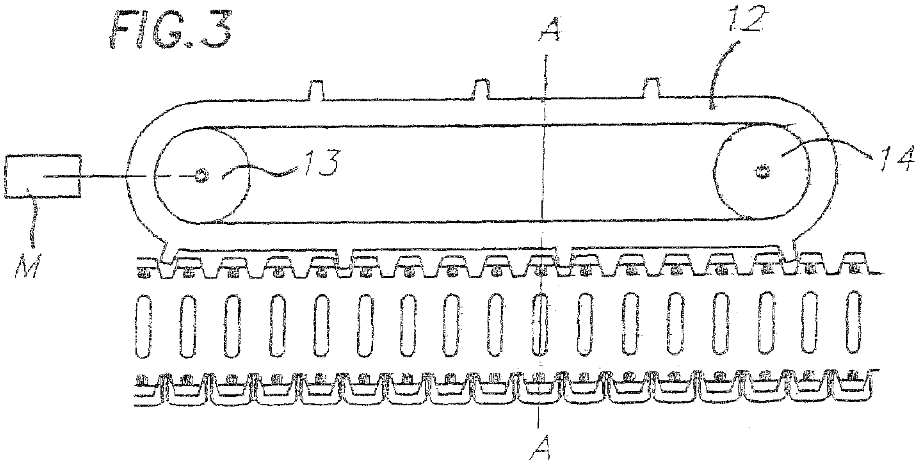
FIG. 3 is a diagrammatic top view of the film equipped with its bowls and the rack drive system.

As shown on FIG. 2, the bowls C embodied by moulding a transparent plastic material, each bowl having a flat parallelpiped-shaped body BB whose bent inward bottom FI constitutes a rolling path 30 for a ferromagnetic ball BE. Opposite this bottom FI, the bowl C has an opening, its two opposing sides $BO_1$, $BO_2$ being extended at a right angle by two respective shoulders R1, R2 each provided with a cylindrical protuberance PC extending on the front and back sides of the body BB. These two protuberances PC are intended to be forcefully engaged in two respective holes TR respectively provided on the two lateral borders of the support film 3. The shoulders R1, R2 have for example the shape of an isosceles trapezium whose large base is integral with the front and back sides of the bowl C. The lateral borders of the support film 3 then have in the interval of the shoulders R1, R2 of the bowls C sets of trapezoidal cuts whose oblique edges are co-linear with the oblique edges of the shoulders R1, R2 of the bowls. Thanks to these provisions, each of the side edges of film 3 present a notched profile whose teeth are accentuated by the edges R1, R2 of the bowls.

Figure 1:
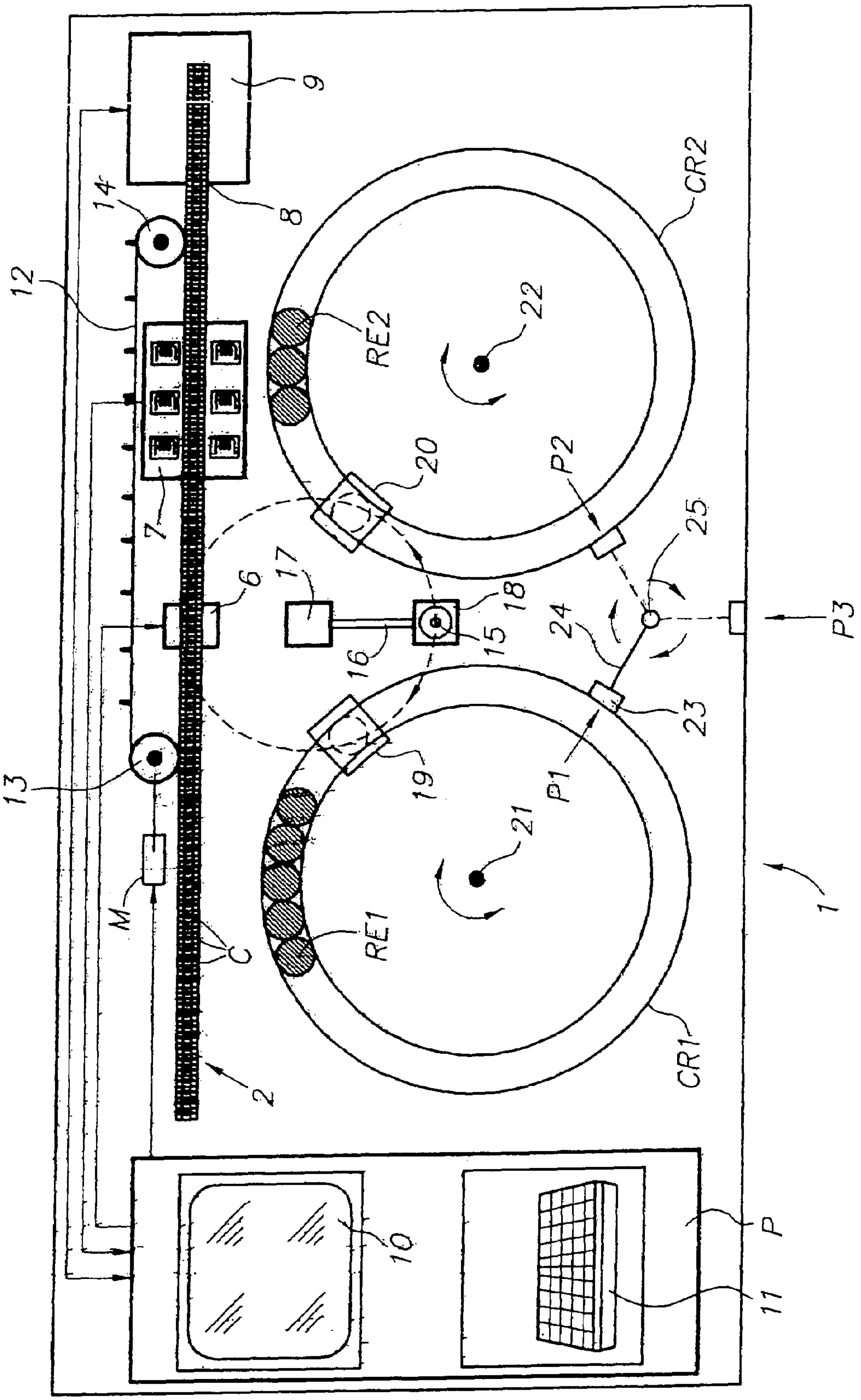
FIG. 1 is a diagrammatic representation of an average-sized automatic analysis device.

The film is flexible and is made of an absorbent material, such as paper. As shown in FIGS. 1-2, above each bowl C, the film 3 is pierced at the top with an oblong orifice 4 extending along the longitudinal axis of the bowls transversally to the run-off axis of the bowls.

Figure 4:
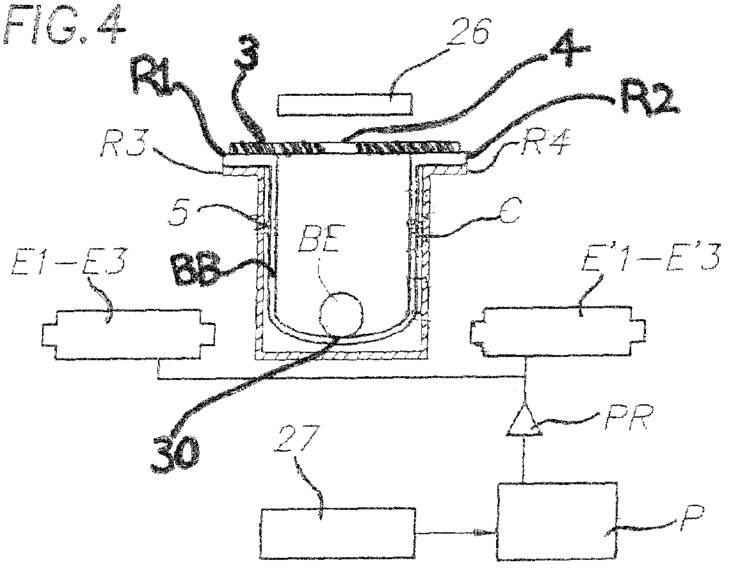
FIG. 4 is a diagrammatic vertical section along section line A-A of FIG. 1.

According to the device shown on FIG. 4, the strip of bowls 2 is guided by a rail 5. This rail has a U-shaped section whose two vertical wings are extended at a right angle by two shoulders R3, R4, the shoulders R1, R2 rest onto the shoulders R3, R4. As shown in FIG. 1, strip 2 passes in succession through a pipette station 6, a detection station 7 and a cutting station 8 at the outlet of which each analysed bowl being recovered in a container 9 provided for this purpose. FIG. 4 also shows that the length of the orifice 4 is over and parallel to the rolling path 30 of ball BE and the width of the orifice 4 is smaller than the diameter of ball BE.

The functioning of these various stations is controlled by a processor P comprising a central unit and peripheral units, such as a screen 10 and keyboard 11 unit.

The driving of the film 3 is ensured by a drive mechanism introducing an endless belt 12 guided at each extremity by rollers 13, 14. This belt comprises a serration whose notches are spaced by a distance equal to a multiple of the width of the bowls (for example 4-5 bowls). These notches have an involute to a circle profile which corresponds to a normal tooth-shaped rack so as to fully gear between the teeth of the serrated profile of the strip; thus, these notches accurately drive the strip of bowls with self-centering and compensation of any possible play.

The pipette station 6 is controlled by an automated vertical height-adjustable pipette 15 so as to be able to assume a lower pipette or rinsing position and an upper position enabling it to move inside a horizontal plane.

This pipette 15 is fixed to one of the extremities of an arm 16 mounted rotating by its other extremity around a vertical spindle 17. The driving in rotation of the arm 16 is ensured by a motor controlled by the processor P.

By means of this particularly simple mechanism, the pipette 15 can be successively brought to the pipette area of the pipette station 6, a diametrically opposite rinsing station 18 equipped with one or several rinsing bowls, and two sampling areas 19, 20 placed symmetrically with respect to the axis passing through the pipette area 6 and the rinsing area 18.

The sampling areas 19, 20 are situated in the path of the receptacles RE1, RE2 borne by two respective carousels CR1, CR2 moving in rotation around two vertical spindles 21, 22 and controlled by two motors controlled by the processor P.

One of these carrousels CR1 is used to contain the receptacles RE1 of the blood samples to be analysed, whereas the other carrousel CR2 contains receptacles RE2 allocated to the various reactive agents able to be used as part of the analyses it is desired to carry out.

Of course, the processor P is programmed so as to control pipette sequences appropriate to the nature of the analyses to be conducted and possibly successively comprising:

- a prior rinsing of the pipette 15,
- the taking of a sample dose contained in one of the receptacles RE1 of the carrousel CR1,
- the injection of this dose into a bowl C situated in the pipette station 6,
- the rinsing of the pipette 15,
- the taking of a reactive agent dose contained in one of the receptacles RE2 of the carrousel CR2,
- the injection of this reactive agent dose into the bowl C,
- the identification of the blood samples to be analysed and that of the reactive agents being carried out automatically by means of a bar code reader 23 able to carry out a reading of the bar codes present on the receptacles RE1, RE2 borne by the carrousels CR1, CR2.

In this example, for these readings, the sole bar code reader 23 is mounted at the extremity of an arm 24 pivoting around a vertical spindle 25 so as to be able to occupy three positions, namely:

- a position P1 for reading the bar codes of the receptacle RE1 of the carrousel CR1,
- a position P2 for reading the bar codes of the receptacle RE2 of the carrousel CR2,
- a position P3 for reading the receptacles placed by the operator in a reading station with a view, for example, of entering the information exploited by the processor within the context of functioning of the device.

The detection station 7 here comprises three successive measuring positions, each comprising (FIG. 4) a pair of coaxial electromagnets E1, E'1-E2, E'2-E3, E'3 situated on both sides of the film (3) in front of the lateral sides of the bowls C.

The station 7 also comprises:

- an infrared light source 26 situated above the bowl,
- an opto-electronic detector in the form of a load transfer detector bar (DTC) 27 situated below the bowls C borne by the film onto which the image of the ball illuminated by the light source is projected.

The use of several measuring positions on the path of the film has the advantage of permitting greater flexibility of operation.

It is to be noted that the light source, which is secured to the rail 5, moreover ensures support via the top of the bowls/film unit so as to avoid the coming out of the rail.

The electromagnets E1, E'1-E2, E'2-E3, E'3 are excited by a power circuit PR controlled by the processor P so as to generate a magnetic pulse field able to drive the ball BE along an alternative movement at the bottom of the bowl C.

The load transfer detector bar 27 which can be a camera is coupled to the processor P which carries out a real time analysis of the image by means of a suitable software so as to measure the amplitude of the oscillations of the ball BE and determine the critical instant when this amplitude falls below a specific threshold (for example 50% of the initial amplitude).

Of course, the processor P counts the time between the moment when the reactive agent has been injected into the bowl C and this critical instant so as to deduce from this a coagulation time.

The movements of the film are synchronised with the operating times of each of the stations of the device and in particular with the magnetic filed pulses generated by the coils.

The pipette station could also be situated at the same location as the measuring station.

Of course, the invention is not limited to the embodiment previously described.

Thus, for example, each infrared source/camera unit could have a field comprising several bowls each excited by a pair of separate electromagnets so as to follow the bowl over a forward movement of several steps with a processor P programmed to simultaneously detect the movements of the balls of different bowls.

The invention claimed is:

1. Device for automatically analysing a liquid sample, this device comprising: a series of bowls for a single use, mobile along a reeling off axis and each comprising a bottom, an upper face opposite the bottom having an opening and two opposing shoulders extending from front and back sides of the bowl approximately in the plane of the opening, the bowls being engaged side by side and joined to each other by a flexible film secured to said shoulders and covering at least partially the openings of said bowls, said flexible film having a series of oblong orifices having spaced apart edges and extending respectively above the openings of said bowls and transversing to said reeling off axis, wherein said spaced apart edges allow insertion of injection and/or sampling means with no contact with edges of the orifice, said device further comprising an optical detection station through which pass said film and said bowls, said station comprising a light source generating a light beam which illuminates the upper face of each bowl present in the station, and an opto-electronic detector placed below said bottom, said film being made of a light diffusing material for rendering the light beam more homogeneous, wherein said light source of said detection station is an infrared light source and said opto-electronic detector comprises a load transfer detector bar.

2. Device according to claim 1, wherein the dimensions of the orifice are determined according to the dimensions of the pipette, its position and the sought-after homogeneity of the intensity of the luminous beams traversing a predetermined working volume of the bowl.

3. Device according to claim 1, wherein the bottom of the bowls constitutes a rolling path of a ball driven by an external magnetic field.

4. Device according to claim 3 wherein the length of said oblong orifice is over and parallel to the rolling path of the ball and the width of the oblong orifice is smaller than the diameter of the ball.

5. Device according to claim 4, wherein the external magnetic field is generated by electromagnetic means placed lateral with respect to the series of bowls in front of their lateral sides.

6. Device according to claim 1, wherein the material constituting the film possesses liquid absorption properties.

7. Device according to claim 1, wherein the series of bowls follow a path passing successively through a pipette station, a detection station and a station for cutting the analysed bowls.

8. Device according to claim 1, wherein analysed bowls are collected in a single container.

9. Device according to claim 1, wherein said shoulders have a shape enabling them to engage between the notches of a drive belt.

10. Device according to claim 9, wherein said shoulders have oblique edges so as to have a shape of an isosceles trapezium whose large base is integral with the bowl.

11. Device for automatically analyzing a liquid sample in a detection station provided with an opto-electronic detector and a light source, said device comprising a series of bowls each having a bottom, an upper face opposite the bottom having an opening and two opposing shoulders extending from front and back sides of the bowl approximately inside the plane of said opening, the bowls being placed side by side and joined to each other by a flexible film having a series of orifices located respectively above said openings, said shoulders having first oblique edges which form an isosceles trapezium having a base thereof integral with the bowl, said film having lateral borders provided between the shoulders of successive bowls with trapezoidal cuts having second oblique edges co-linear with said first oblique edges of said shoulders, wherein said light source of said detection station is an infrared light source and said detector comprises a load transfer detector bar.

12. Device for automatically analyzing a liquid sample, this device comprising a series of bowls mobile along a reeling off axis and each comprising a bottom, an upper face opposite the bottom having an opening and two opposing shoulders extending from front and back sides of the bowl in the plane of the opening the bowls being placed side by side and joined to each other by a flexible film secured to said shoulders and covering at least partially the opening of said bowls, said device further comprising an optical detection station having a light source generating a light beam which illuminates the upper face of the bowl and an opto-electronic detector placed below the bottom, said light source having a support which is secured to a rail which supports said bowls and said film via the top, wherein said light source of said detection station is an infrared light source and said detector comprises a load transfer detector bar.

* * * * *

UNITED STATES PATENT AND TRADEMARK OFFICE

CERTIFICATE OF CORRECTION

PATENT NO. : 7,507,377 B2
APPLICATION NO. : 10/503239
DATED : March 24, 2009
INVENTOR(S) : Rousseau et al.

It is certified that error appears in the above-identified patent and that said Letters Patent is hereby corrected as shown below:

On the title page,

[*] Notice: Subject to any disclaimer, the term of this patent is extended or adjusted under 35 USC 154(b) by (277) days Delete the phrase “by 277 days” and insert -- by 853 days --

Signed and Sealed this

Sixth Day of April, 2010

David J. Kappos
*Director of the United States Patent and Trademark Office*